United States Patent
Poillucci

(10) Patent No.: US 8,678,984 B1
(45) Date of Patent: Mar. 25, 2014

(54) HAND, WRIST, ARM AND FINGERS THERAPY AND EXERCISING DEVICE

(76) Inventor: Gary Poillucci, Watertown, MA (US)

( * ) Notice: Subject to any disclaimer, the term of this patent is extended or adjusted under 35 U.S.C. 154(b) by 667 days.

(21) Appl. No.: 12/932,069

(22) Filed: Feb. 17, 2011

Related U.S. Application Data

(63) Continuation-in-part of application No. 12/026,879, filed on Feb. 6, 2008, now abandoned.

(51) Int. Cl.
  *A63B 21/02* (2006.01)
  *A63B 23/14* (2006.01)
  *A63B 23/16* (2006.01)
  *A63B 21/045* (2006.01)
  *A61F 5/00* (2006.01)

(52) U.S. Cl.
  USPC .............. 482/124; 482/44; 482/47; 482/127; 602/21

(58) Field of Classification Search
  USPC .................. 482/10–11, 44–50, 79–80, 91–92, 482/121–122, 124, 127, 129–130; 601/23, 601/33, 40; 602/20–21
  See application file for complete search history.

(56) References Cited

U.S. PATENT DOCUMENTS

| | | | | |
|---|---|---|---|---|
| 2,832,334 | A | * | 4/1958 | Whitelaw ........................ 601/33 |
| 4,039,183 | A | * | 8/1977 | Sakurada ........................ 482/46 |
| 4,310,154 | A | * | 1/1982 | Kauffman ...................... 482/46 |
| 4,589,655 | A | * | 5/1986 | Ammon ......................... 482/46 |
| 5,100,126 | A | * | 3/1992 | Liou .............................. 482/46 |
| 5,358,471 | A | * | 10/1994 | Klotz ............................ 602/21 |
| 5,364,323 | A | * | 11/1994 | Liu ................................ 482/45 |
| 2009/0197741 | A1 | * | 8/2009 | Poillucci et al. ................ 482/44 |

* cited by examiner

*Primary Examiner* — Oren Ginsberg
(74) *Attorney, Agent, or Firm* — William Nitkin

(57) ABSTRACT

A hand, wrist, arm and fingers therapy and exercising device which includes a push bar pivotally connected to a base and a wrist support portion. The push bar is moveable between a neutral position, an extended position and a stretching position. The push bar includes finger cams at the end thereof for exercise of the fingers.

14 Claims, 2 Drawing Sheets

HAND, WRIST, ARM AND FINGERS THERAPY AND EXERCISING DEVICE

This application is a continuation-in-part of my previous application entitled Hand, Wrist and Arm Therapy and Exercising, application Ser. No. 12/026,879, filed Feb. 6, 2008, now abandoned.

BACKGROUND OF THE INVENTION

1. Field of the Invention

The device of this invention resides in the field of exercise and therapy devices and more particularly relates to an exercise and therapy device for the fingers, hand, wrist and arm of the user.

2. History of the Prior Art

Several common medical conditions have been connected to tasks involving highly repetitive manual acts or acts necessitating wrist bending or stressful wrist and hand postures. Such medical conditions can also arise from injuries such as from accidents. One such condition is carpal tunnel syndrome (CTS) in which the median nerve is compressed or swollen at the wrist, leading to chronic wrist pain, numbness and muscle weakness in the forearm and hand.

It is estimated that 10% of adults suffer from CTS. Common activities that have been identified as contributing to CTS include construction, typing, text messaging, sports training, cycling, crafting, push mowing and use of power tools. CTS is also thought by some medical professionals to cause heightened symptomatic responses among those suffering from osteoporosis, osteoarthritis, rheumatoid arthritis and conditions brought on by nerve and joint damage.

Similar difficulties are often experienced by those who have suffered a stroke or hand, wrist or arm trauma or who suffer from arthritis. While these conditions can make the simplest of tasks difficult or painful, a measure of relief is afforded through improved circulation, stretching of tendons, muscles and joints and strengthening of muscles.

One effective CTS preventative measure recommended by OSHA and health professionals is to take frequent breaks from repetitive activities. Software programs such as WORKRAVE™ AND XWRITS™ are available to remind users to take breaks and stretch their wrists during computer keyboard usage. Health professionals have suggested wearing wrist braces at night and during repetitive activities. Professional physical therapy techniques include soft tissue massage, conservative stretches and exercises to encourage improved circulation.

Accordingly, there is a need for a convenient personal wrist therapy device that allows CTS sufferers to regularly stretch and exercise affected areas of the fingers, hand, wrist and arm during regular breaks from repetitive movements.

SUMMARY OF THE INVENTION

One aspect of the invention features an exercise apparatus which includes a base, a movable wrist support connected to the base and a push bar pivotally connected to the base and biased towards a neutral position to be engaged by extended fingers of the user to move the bar from the neutral position. The device further includes a tension adjustor for changing the amount of force necessary to move the bar from the neutral position to another position. The tension adjustor can be set for a locked position of the push bar. The adjustor serves to adjust the device as to distances between parts of the device and its interaction with the user to enable the device to fit each user. Adjustable device settings allow the user to adjust the resistance against pressure applied by the user for the desired effect.

The device further includes a plurality of sprung finger cams extending from the push bar for exercising individual or multiple fingers. The finger cams can be rotated or locked together to be rotated in any desired combination. The finger cams can be rotated independent of rotation of the push bar. The spring tension of the finger cams can have adjustable resistance to movement by the user, and the finger cams can be positioned at different distances from the user depending on the size of the user's hand and what portion of the hand and/or fingers are to be exercised.

In some cases, a magnet, heater, removable and replaceable microwavable pad, ice pack, electric stimulus electrode or vibrator can be positioned adjacent to the wrist support to provide additional therapeutic effects.

In some embodiments of the invention, the push bar and wrist pivot are constructed and arranged such that activation of the push bar by a user allows both linear wrist movement and angular wrist movement because of the user's ability to rotate the hand due to the wrist-pivoting ability of the device.

The locked position of the push bar can be used to hold and stretch the wrist at a predetermined position, for example, at the end of the natural range of wrist motion. The push bar is movable from the neutral position in both upward and downward directions to exercise and stretch both flexor and extensor muscle groups. The push bar can also be lengthened or shortened to accommodate both extended and gripping finger positions, and the push bar can be adjustable to different radial distances from the wrist pivot to accommodate different hand sizes or hand positions. The push bar can be telescoping sprung to provide a gripping exercise range of movement. Thus the push bar can be locked in a stretching position different from the neutral position to provide extended stretching of the wrist, fingers, arm including musculature at the elbow; and such device can include adjusting the location of the neutral position of the push bar.

In some implementations the wrist support is rotatably secured within a ring or partial ring connected to the base to provide a range of forearm rotation during movement of the push bar with the ability to exercise the arm in different angles of rotation within the device of this invention.

Another aspect of the invention features an exercise apparatus including a forearm brace, a push bar pivotally connected to the forearm brace and biased towards a neutral position and wherein the neutral position of the push bar can be adjusted substantially perpendicular to the forearm to stretch the wrist at or beyond the natural flexural range of wrist extension.

Attachment of the exercise device to a forearm brace allows a user to exercise without having to remain seated or positioned next to a support surface. Such attachment would even allow a user to combine exercise sessions with other activities. In some implementations the brace is arranged and constructed to engage both the top and bottom of the forearm to provide bi-directional support and resistance.

Another aspect of the invention features a method of using an exercise apparatus including the steps of positioning a wrist on a wrist support connected to a base, engaging with fingers a push bar pivotally connected to the base at a wrist pivot and biased towards a neutral position, and moving the push bar from the neutral position by flexing and extending the hand, wrist or arm muscles, singularly or in combination, while at the same time exercising the wrist, hand, elbow, shoulder, and fingers on the finger cams, each individually or together. In some cases the step of securing the wrist to the wrist support is included.

Implementation and applications of the invention provide benefits and advantages of wrist therapy and exercise in a compact, portable, personal use exercise and therapy station. It is believed that stretching and other therapeutic effects provided by implementations and applications of the invention will afford users a measure of relief from CTS and other hand, wrist, elbow and arm related conditions.

DESCRIPTION OF THE PREFERRED EMBODIMENT(S)

Figure 1:
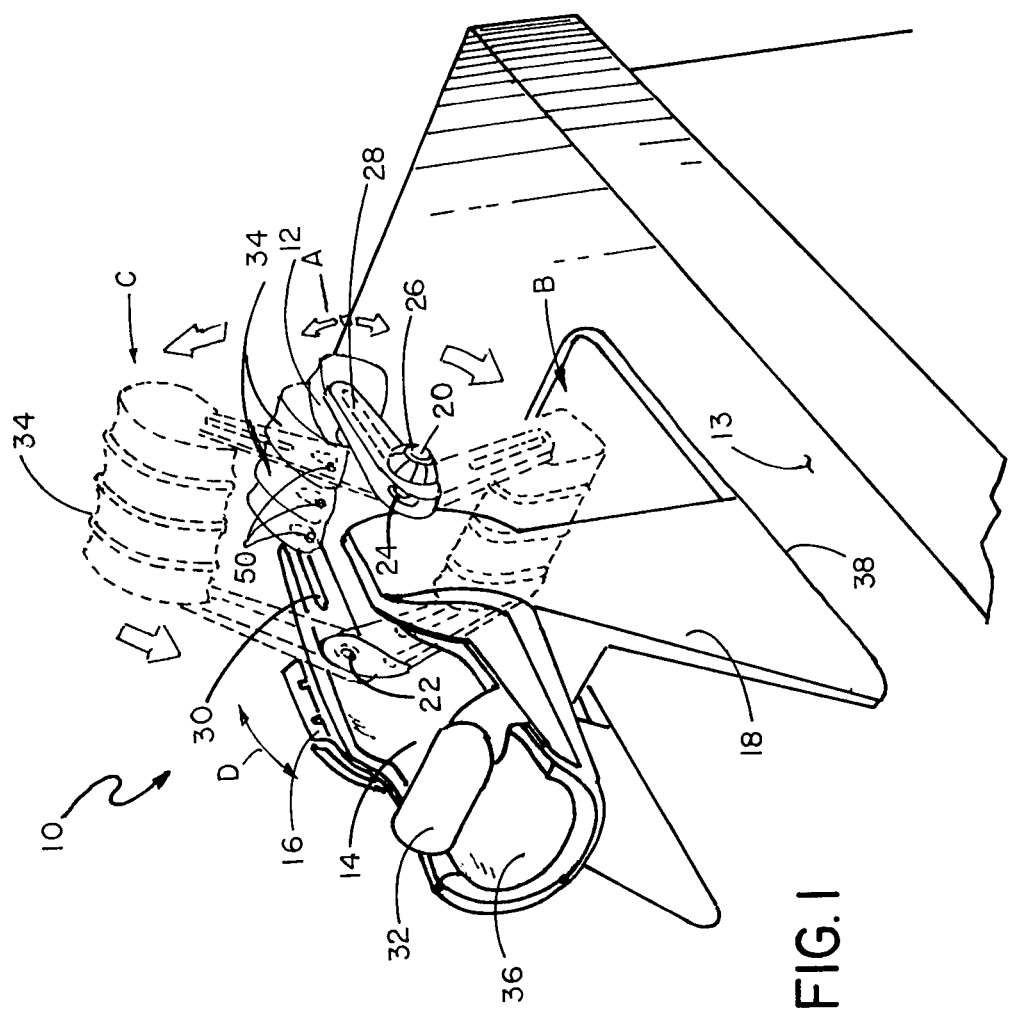
FIG. 1 illustrates a perspective view of the device of this invention resting on a surface.

FIG. 1 is a perspective view of hand, arm, wrist and fingers exercise/therapy device 10 featuring push bar 12 positioned forward of wrist support 14 on base 18. Push bar 12, which is generally U-shaped, is pivotally connected to base 18 at first and second wrist pivots 20 and 22 and is sprung or biased towards a resting or neutral position A. Push bar 12 is positioned to be moved by the extended fingers of a user having his or her wrist resting on wrist support 14.

In the embodiment shown in FIG. 1, push bar 12 is configured or adjusted to be engaged by the fingers in the extended position, or alternatively in a gripping position. In some cases push bar 12 can be padded, contoured or otherwise configured to increase user comfort. Push bar 12 is movable in one or two directions from the neutral position A. In some implementations push bar 12 is adjusted to move from the neutral position A or to lock push bar 12 in the stretching position C. For example, a user can lock push bar 12 at an upward extreme to position C to stretch the wrist at or beyond the natural range of wrist motion. The locked position is adjustable, for example, through a range of stretching positions as part of an ongoing physical therapy regiment. Locking of push bar 12 can be accomplished with a friction device, shear device or other resistance mechanism, such as tightenable lock nuts at first and second wrist pivots 20 and 22, suitable to fix push bar 12 at a desired position relative to base 18.

Base 18 can be injected molded using plastic or can be formed from wood or metal. Base 18 is depicted as including lower portion 38 for engaging the underside of a table or support surface 13 during use. In other embodiments base 18 can include a weighted base, a rubber non-slip lower surface, a suction cup, table mount bracket or other well-known structure to help maintain base 18 in place during use. Base 18 can alternatively be mounted on a dedicated adjustable stand to provide for height adjustment for use with different therapy patients or for switching between user while standing, sitting or laying down.

Base 18 further can include a clamp for securing exercise/therapy device 10 to a support structure, such as an office desk or table. In some cases, clamping is accomplished by spring-loaded jaws, interference fits with high friction members and the like. Still in other embodiments of base 18 a clamping flange extending around the edge and under the table can serve as an under-edge table brace to simply prevent forward and upward movement of base 18 during forward and downward movement of push bar 12.

With continued reference to FIG. 1, a method of using exercise/therapy device 10 includes the steps of positioning base 18 a comfortable distance from the user's body, positioning the user's wrist on wrist support 14, engaging push bar 12 with the user's fingers, and pushing push bar 12 by the fingers' action on finger cams 34 from the neutral position A. Device 10 can be used for the fingers only or for hand, wrist, elbow and shoulder only exercises or any combination of exercises for the above-listed body parts. While push bar 12 is depicted as configured for pushing using the flexor muscles of the user, push bar 12 can also be configured for pulling, for example using the extensor muscles of the user. Push bar 12 is movable through a comfortable range of motion and adjustable to urge or hold the user's hand in a more extreme position, for example, for stretching or as part of physical therapy. Push bar 12 is configured to provide either a constant resistance or a graduated resistance to movement from the neutral position.

First and second wrist pivots 20 and 22 can include first spring 24 and an equivalent second spring interposed between push bar 12 and base 18 to bias push bar 12 towards neutral position A. Any number of different types of locations of spring 24 can be incorporated to generate a resistive force to be overcome by a user during use of the device. While first and second wrist pivots 20 and 22 are depicted as a rotating member with spring 24 providing a resistive force, in other embodiments first wrist pivot 20 can be fixed with respect to base 18, and push bar 12 can be configured as a flexible member such that push bar 12 is elastically flexed about first and second wrist pivots 20 and 22. First and second wrist pivots 20 and 22 are depicted as attaching to the outer sides of base 18. In other embodiments first and second wrist pivots 20 and 22 can be located on the inner sides of base 18 or within channels formed in base 18. Push bar 12 can be removable or interchangeable by separating first and second wrist pivots 20 and 22 from base 18.

Referring further to FIG. 1, exercise/therapy device 10 includes four individual sprung finger cams 34 rotatably connected to push bar 12 and engaged by fingers to provide strengthening and stretching of the finger muscles. A user can position his/her wrist with the palm facing up or down for comfort as desired during operation of the device. Finger cams 34 can be constructed of different lengths to accommodate different finger lengths, and push bar 12 with finger cams 34 can be adjustable to accommodate different hand sizes. As similarly described with regard to adjustor 26, finger cam adjustor 50 can be provided for finger cams 34 for spring force adjustments, range of motion adjustments, neutral positioning and the like. Push bar 12 is movable about first and second wrist pivots 20 and 22 between a neutral position A, a flexed position B and an extended position C.

FIG. 1 also illustrates exercise/therapy device 10 showing wrist support 14 rotatably secured within slip ring 16 connected to base 18. In this embodiment a user is not limited to palm up or palm down hand orientation but can rotate wrist support 14 at least 270 degrees rotation, as indicated by arrow D, to operate the device with the palm and wrist in any desired orientation. Accordingly, a user can rotate his/her forearm before or while extending his/her wrist between positions A, B and C.

Referring further to FIG. 1, first and second wrist pivots 20 and 22 can be provided with an adjustor 26 for adjusting various push bar settings, such as the degree of resistive force or bias provided by spring 24. Adjustor 26 is a dial configured to wind or unwind spring 24. Adjustor 26 can alternatively or additionally serve to adjust the location of the neutral position, i.e. the resting position of spring bar 12 relative to base 18 or the location of a locked stretching position. Adjustor 26 serves in other cases to adjust the position of various stop members 48 associated with first and second wrist pivots 20 and 22 to define a desired range of motion of push bar 12. For example, stop members can be used to limit the range of push bar movement to a prescribed range of wrist movement for physical therapy. Alternatively, push bar settings can be adjusted to provide greater resistance in one direction than another or to select between constant and graduated resistance.

Still in other cases, adjustor 26 serves to lock push bar 12 relative to base 18, for example, to provide a fixed stretching position for a user or to lock push bar 12 in a stowed or collapsed position adjacent to base 18. Thus the neutral position of push bar 12 is adjustable within a range of motion of the user's wrist or for stretching at or beyond the end of a comfortable range of movement. For example, push bar 12 can be sprung towards an extreme upwards position but can be temporarily locked in a lower position to allow a user to position his or her wrist and hand before releasing push bar 12 to stretch the hand upwards. The movement of the various components can be automated to mechanically stretch the fingers, hand, wrist or arm of the user. In an alternative implementation a wrist support is rotatably secured within slip ring 16 connected to the base to allow a range of arm rotation of at least 270 degrees while the user extends his/her wrist between positions A, B and C.

Additional adjustment can be provided to fit device components to a given user or to otherwise render exercise/therapy device 10 more ergonomic or effective. For example, push bar 12 is adjustable in some cases by sliding or telescoping, for example within first and second slots 28 and 30, as seen in FIG. 1, to adjust the radial distance from base 18, thus allowing a single device to be used for a range of hand sizes or for a range of hand positions, such as with push bar 12 engaged by extended fingers or with push bar 12 gripped to varying degrees by the user's fingers. Push bar 12 can be telescopingly sprung such that push bar 12 can be compressed in a gripping motion. Combined radial and telescoping mobility provide a wider range of possible exercise and stretching positions.

Other device adjustments, such as varying the height of base 18, angle of wrist support 14 and the like can be provided in various examples. Adjustability of push bar length or angle, base height or angle, and wrist support arrangement can be provided by varying any number of sliding, graduated or incremental positional relationships between any of the components described herein.

Base 18 is provided with wrist strap 32 over wrist support 14. Wrist strap 32 allows a user to further immobilize his or her arm to better isolate muscles for strengthening or stretching. For example, wrist strap 32 allows a user to move push bar 12 in both upward and downward extensions without inadvertently lifting his or her arm from wrist support 14. For example, first and second wrist pivots 20 and 22 are shown at a height proportionate to the distance between the wrist and fingertips.

Base 18 and wrist support 14 can also include eccentric weight vibrators, other types of vibrators, heater, heat pack, ice pack or electric stimulus electrode and can be powered by batteries, chemical reaction or a plug-in adapter. For example, heat packs, ice packs or electrodes can be provided on wrist support 14 or can be worn by the user during stretching. Thus, a user can benefit from the combined therapeutic effects of stretching, vibration, icing, heating and stimulating his or her hand, wrist and arm during physical therapy or during breaks from repetitive or stressful activities.

Neutral position A can be adjusted somewhere between the depicted position A and B. For example, neutral position A can be adjusted such that push bar 12 extends substantially horizontal to a support surface so that a user can overcome the restorative force of spring 24 with either an upward or downward deflection of the wrist. The user can position his/her fingers on either side of push bar 12 to select upward or downward extensions. Alternatively, push bar 12 can be fitted with a finger loop, strap or cup to permit alternating bi-directional extensions without repositioning of the fingers on push bar 12.

Referring further to FIG. 1, exercise/therapy device 10 can include wrist pad 36 disposed over wrist support 14. Wrist pad 36 can be a removable microwavable heating pad or ice pack used to increase the therapeutic effect of the exercise/therapy. Wrist pad 36 can be a flexible solid, a gel or a contained liquid or granular layer selected to retain heat over the course of a physical therapy session.

Figure 2:
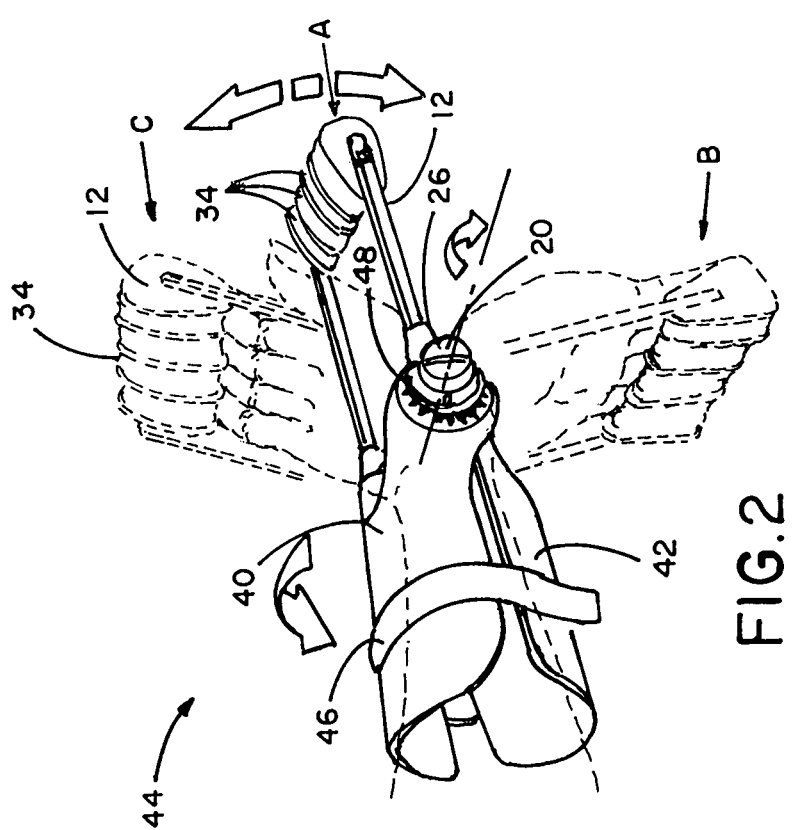
FIG. 2 illustrates a perspective view of the embodiment of the device that is retained on the forearm of the wearer and which embodiment does not require a base for resting on a surface.

FIG. 2 illustrates a perspective view of an alternate embodiment 44 of this invention that is retained on the forearm of the wearer and which does not require a surface retention base. The forearm brace consists of first and second brace portions 40 and 42 disposed, respectively, on the upper and lower portions of the user's arm. Thus the forearm serves as the support or base for the device and serves to resist the counter-movement of the device in response to a movement of U-shaped push bar 12. The wrist support is formed by a forward section of lower brace position 42. Removal of strap 46 allows the user to separate first and second brace portions 40 and 42 to place device on the forearm. Strap 46 is then tightened and secured to hold upper and lower brace portions 40 and 42 in a closed position on the forearm. Accordingly, the device need not be clamped to, or rested on, a stationary surface but can be constructed as a fully portable personal exercise and therapy device for use in any orientation. Push bar 12 is depicted in a first neutral position A, with second extended position B and a third stretching position C shown in dashed lines. Position C is adjustable by a user for a desired degree or range of stretching. Wrist pivot 20 includes an adjustor 26 for setting the resistance of push bar 12 and/or the range or location of positions A, B and C of push bar 12. Push bar 12 has finger cams 34 which can be padded, contoured or otherwise configured to increase user comfort. The embodiment of the invention illustrated in FIG. 2 operates similarly to that of the embodiment shown in FIG. 1.

Although the present invention has been described with reference to particular embodiments, it will be apparent to those skilled in the art that variations and modifications can be substituted therefor without departing from the principles and spirit of the invention.

I claim:

1. An exercise and therapy apparatus for use on or off a support surface by a user having an arm, flexor and extensor muscle groups, a forearm having a top and bottom, a wrist, a shoulder, an elbow and a hand having a palm and fingers, comprising:

a base having a concave wrist support portion that support the user's wrist, said base being arranged and constructed to engage the bottom of the forearm at the user's wrist, said base, when resting on said support surface being of sufficient height to allow both linear and angular wrist movement without the hand contacting said support surface;

a push bar pivotally connected to said wrist support portion, said push bar sprung and biased towards a resting neutral position wherein said push bar can be moved through a range of positions by hand movement to a selected position, said push bar movable to be substantially perpendicular in both directions to the orientation of the user's forearm for stretching the wrist beyond the wrist's natural extension range, said push bar's movement being adjustable for providing either a constant or gradual resistance to movement by said user's hand from said neutral position;

a tension adjustor for changing the amount of force necessary to move said push bar by said hand's pushing or pulling from said neutral position both in an upwards and downward direction for exercising said flexor and extensor muscle groups, said tension adjustor being able to lock said push bar in a selected position; and further including a plurality of individually sprung finger cams of selected lengths extending from said push bar for exercising individual or multiple fingers, said finger cams can be rotated or locked in any desired combination with the spring tension of each finger cam being independently adjustable in resistance to movement.

2. The device of claim 1 wherein said push bar is further adjustable to different radial distances from said wrist support portion for accommodating different hand sizes or hand positions, said push bar being telescopingly sprung to provide a range of gripping exercise movements.

3. The device of claim 2 wherein said wrist support portion is rotatable from a palm down position to a palm up position and vice versa through 270 degrees.

4. The device of claim 3 further including attachment means for attaching said base to said support surface.

5. The device of claim 4 further including adjustable stop members for allowing for varying degrees of push bar rotation.

6. The device of claim 5 wherein said finger cams have a neutral position aligned with said neutral position of said push bar, said finger cams being movable either up or down, respectively, by said fingers of said user contacting said finger cams from either above or from below.

7. The device of claim 6 wherein said finger cams further include tension adjustor means for changing the amount of force necessary for said user's fingers to move said finger cams either by pushing up or pulling down for exercising, respectively, said flexor or extensor muscle groups in said fingers and arm as well as separately or together, the shoulder, elbow, wrist, hand and fingers.

8. The device of claim 7 further including secondary treatment means disposed in said wrist support portion, said secondary treatment means selected from the group of cushioning means, heating means, cooling means, vibration means, electrical stimulation means and magnetic stimulation means.

9. An exercise and therapy apparatus for use away from a support surface by a user having an arm, flexor and extensor muscle groups, a forearm having a top and bottom, a wrist, and a hand having a palm and fingers, comprising:

a forearm brace having a lower brace portion and an upper brace portion, said lower brace portion providing a concave wrist support portion that supports the user's wrist, said forearm brace being arranged and constructed to engage both the bottom of the user's forearm and the user's wrist and top of the forearm to provide bi-directional support and resistance, said forearm brace allowing both linear and angular wrist movement;

a push bar pivotally connected to said forearm brace, said push bar being sprung and biased towards a resting neutral position wherein said push bar can be moved through a range of positions by hand movement to a selected position, said push bar movable to be substantially perpendicular in both directions to the orientation of the user's forearm for stretching the wrist beyond the wrist's natural extension range, said push bar's movement being adjustable for providing either a constant or gradual resistance to movement by said user's hand from said neutral position;

a tension adjustor for changing the amount of force necessary for the user to move said push bar by said hand's pushing or pulling from said neutral position both in an upwards and downward direction for exercising said flexor and extensor muscle groups, said tension adjustor being able to lock said push bar in a selected position;

wherein said push bar is further adjustable to different radial distances from said forearm brace for accommodating different hand sizes or hand positions, said push bar being telescopingly sprung to provide a range of gripping exercise movements; and further including a plurality of individually sprung finger cams of selected lengths extending from said push bar for exercising one or more fingers, said finger cams can be rotated or locked in any desired combination with the spring tension of each finger cam being independently adjustable.

10. The device of claim 9 wherein said forearm brace is rotatable from a palm down position to a palm up position and vice versa through 270 degrees.

11. The device of claim 10 further including adjustable stop members for allowing for varying degrees of push bar rotation.

12. The device of claim 11 wherein said finger cams have a neutral position aligned with said neutral position of said push bar, said finger cams being movable either up or down, respectively, by said fingers of said user contacting said finger cams from either above or from below.

13. The device of claim 12 wherein said finger cams further include tension adjustor means for changing the amount of force necessary to move said finger cams either by pushing up or pulling down for exercising, respectively, said flexor or extensor muscle groups in said fingers and arm as well as separately or together, the shoulder, elbow, wrist, hand and fingers.

14. The device of claim 13 further including secondary treatment means disposed in said forearm brace, said secondary treatment means selected from the group of cushioning means, heating means, cooling means, vibration means, electrical stimulation means and magnetic stimulation means.

* * * * *